United States Patent
Boudec et al.

(10) Patent No.: US 6,768,044 B1
(45) Date of Patent: Jul. 27, 2004

(54) CHIMERIC HYDROXYL-PHENYL PYRUVATE DIOXYGENASE, DNA SEQUENCE AND METHOD FOR OBTAINING PLANTS CONTAINING SUCH A GENE, WITH HERBICIDE TOLERANCE

(75) Inventors: Philippe Boudec, Lyons (FR); Hélène Bourdon, Ecully (FR); Florence Dumas, Fleurieu sur Saone (FR); Matthew Rodgers, Ongas (GB); Alain Sailland, Lyons (FR)

(73) Assignee: Bayer CropScience SA, Lyons (FR)

( * ) Notice: Subject to any disclaimer, the term of this patent is extended or adjusted under 35 U.S.C. 154(b) by 0 days.

(21) Appl. No.: 09/567,615

(22) Filed: May 10, 2000

(51) Int. Cl.$^7$ .............................. A01H 5/00; A01H 5/10; C12N 15/29; C12N 15/82
(52) U.S. Cl. .................... 800/300; 435/320.1; 435/468; 435/419; 435/430; 536/23.2; 536/23.4; 536/23.6; 800/278; 800/298; 800/300.1; 800/312; 800/320
(58) Field of Search ............................... 536/23.4, 23.2, 536/23.6, 23.7, 23.74; 435/320.1, 468, 418, 419, 430; 800/278, 287, 288, 300, 306, 312, 314, 320, 320.1, 320.2

(56) References Cited

U.S. PATENT DOCUMENTS 6,268,549 B1 * 7/2001 Sailland et al. ............. 800/295

FOREIGN PATENT DOCUMENTS

| EP | 0 252 666 A2 | 1/1988 |
|---|---|---|
| WO | WO 96/32484 | 10/1996 |
| WO | WO 96/38567 | 12/1996 |
| WO | WO 97/27285 | 7/1997 |
| WO | WO 98/04685 | * 2/1998 |

OTHER PUBLICATIONS

Gora et al, 1999, Archives of Biochemistry and Biophysics, 362(2): 231–240.*
GenBank Accession No. AAC49815, Garcia et al, Feb. 23, 1997.*
Carrington et al., Cap–Independent Enhancement of Translation by a Plant Potyvirus 5' Nontranslated Region. *J. Virol.*, 1990, 64, 1590–1597.
Lee et al., The C–terminal of rat 4–hydroxyphenylpyruvate dioxeganase is indispensable for enzyme activity. *FEBS Letters*, 1996, 393, 269–272.
Garcia et al., Subcellular localization and purification of a p–hydroxyphenylpyruvate dioxygenase from cultured carrot cells and characterization of the corresponding cDNA. *Biochem J.*, 1997, 325, 761–769.

* cited by examiner

*Primary Examiner*—Amy J. Nelson
*Assistant Examiner*—David H Kruse
(74) *Attorney, Agent, or Firm*—Connolly Bove Lodge & Hutz LLP

(57) ABSTRACT

The invention concerns a nucleic acid encoding a chimeric hydroxyphenyl pyruvate dehydrogenase (HPPD) enzyme formed from a nucleic acid encoding the N-terminal portion of a first plant HPPD in combination with nucleic acid encoding the C-terminal portion of a second plant HPPD, wherein the N-terminal portion and the C-terminal portion are separated by a linker peptide. The nucleic acid can be used to transfom a cell or an organism, such as a plant, to provide tolerance to herbicides. The invention also concerns methods of making and using plants transformed with the nucleic acid.

34 Claims, 5 Drawing Sheets

```
Mus musculus                 ------MTTYNN--KGPKPERG---------------------RFLHFHS
Coccidioides immitis         MAPAADSPTLQ-----PAQPSD-------------LN------QYRGYDH
Mycosphaerella graminicola   MAPGALLVTSQNGRTSPLYDSDGYVP---APAALVVGGE---VNYRGYHH
Hordeum vulgare              MPPTPTTPAA-TGAAAAVTPEHARP----HR-MVRFNPRSDRFHTLSFHH
Zea mais                     MPPTPTAAAAGAAVAAASAAEQAAFRLVGHRNFVRFNPRSDRFHTLAFHH
Arabidopsis thaliana         MGHQNAAVSE-NQNHDDGAASSPGFKLVGFSKFVRKNPKSDKFKVKRFHH
Daucus carota                MGKK-QSEAE-ILSSNSSNTSPATFKLVGFNNFVRANPKSDHFAVKRFHH
Streptomyces avermitilis     ----MTQTTHHT----PDTARQADP-----------------FPVKGMDA
Pseudomonas fluorescens      -----MADLYEN-------PMG---------------------LMGFEF P. fluorescens numbering       |        |
                               1        10

Mus musculus                 VTFWVGNAKQAASFYCNKMGFEPLAYRGLETGSREVVSHVIKRGKIVFVL
Coccidioides immitis         VHWYVGNAKQAATYYVTRMGFERVAYRGLETGSKAVASHVVRNGNITFIL
Mycosphaerella graminicola   AEWWVGNAKQVAQFYITRMGFEPVAHKGLETGSRFFASHVVQNNGVRFVF
Hordeum vulgare              VEFWCADAASAAGRFAFALGAPLAARSDLSTGNSAHASQLLRSGSLAFLF
Zea mais                     VELWCADAASAAGRFSFGLGAPLAARSDLSTGNSAHASLLLRSGSLSFLF
Arabidopsis thaliana         IEFWCGDATNVARRFSWGLGMRFSAKSDLSTGNMVHASYLLTSGDLRFLF
Daucus carota                IEFWCGDATNTSRRFSWGLGMPLVAKSDLSTGNSVHASYLVRSANLSFVF
Streptomyces avermitilis     VVFAVGNAKQAA-HYSTAFGMQLVAYSGPENGSRETASYVLTNGSARFVL
Pseudomonas fluorescens      IELASPTPNTLEPIFEIMGFTKVATHR-----SKD--VHLYRQGAINLIL
                                     :          :         .       :        :::

P. fluorescens numbering      |          |          |
                              20   30    40         50

Mus musculus                 CSALN-----------PWN--------KEMGDHLVKHGDGVKDIAFEVEDC
Coccidioides immitis         TSPLR-SVEQA---SRFP--EDEALLKEIHAHLERHGDGVKDVAFEVDCV
Mycosphaerella graminicola   TSPVRSSARQT---LKAAPLADQARLDEMYDHLDKHGDGVKDVAFEVDDV
Hordeum vulgare              TAPYANGCDAA------TASLPSFSADAARRFSADHGIAVRSVALRVADA
Zea mais                     TAPYAHGADAA------TAALPSFSAAAARRFAADHGLAVRAVALRVADA
Arabidopsis thaliana         TAPYSPSLSAGEIKPTTTASIPSFDHGSCRSFFSSHGLGVRAVAIEVEDA
Daucus carota                T PYSPSTTTSSCS----AAIPSFSASGFHSFAAKHGLAVRAIALEVADV
Streptomyces avermitilis     T   K--P--A---TPWG---------HFLADHVAEHGDGVVDLAIEVPDA
Pseudomonas fluorescens      NKSPH------------S---------VASYFAAEHGPSVCGMAFRVKDS
                                                        .   **  .*   :*:.*

P. fluorescens numbering     |                          |         |
                             60                         70        80
```

FIG 1

```
Mus musculus                 DHIVQKARBRGAKIVREPWVEQDKFGKVKFAVLQTYGDTTHTLVEKINYT
Coccidioides immitis         ESVFSAAVRNGAEVVSDVRTVEDEDGQIKMATIRTYGETTHTLIERSGYR
Mycosphaerella graminicola   LAVYENAVANGAESVSSPHTDSCDEGDVISAAIKTYGDTTHTPIQRTTYT
Hordeum vulgare              AEAFRASRRRGARPAFAPVDLGRG---FAFAEVELYGDVVLRFVSHPDGT
Zea mais                     EDAFRASVAAGARPAFGPVDLGRG---FRLAEVELYGDVVLRYVSYPDGA
Arabidopsis thaliana         ESAFSISVANGAIPSSPPIVLNEA---VTIAEVKLYGDVVLRYVSYKAED
Daucus carota                AAAFEASVARGARPASAPVELDDQ---AWLAEVELYGDVVLRFVSFGREE
Streptomyces avermitilis     RAAHAYAIEHGARSVAEPYELKDEHGTVVLAAIATYGKTRHTLVDRTGYD
Pseudomonas fluorescens      QKAYKRALELGAQPIHIETGPMELN----LPAIKGIGGAPLYLIDRFGEG
                                   :   **                  . :   * .   :.
                              !         !         !             !         !
P. fluorescens numbering      90       100       110           120       130

Mus musculus                 G---RFLPGFEAPTYKDTLLPKLPRCNLEIIDHIVGNQPDQEMQSASEWY
Coccidioides immitis         G---GFMPGYRMESNADATSKFLPKVVLERIDHCVGNQDWDEMERVCDYY
Mycosphaerella graminicola   G---PFLPGYRSCTTVDSANKFLPPVNLEAIDHCVGNQDWDEMSDACDFY
Hordeum vulgare              D--VPFLPGFEGVTNPDAVD-----YGLTRFDHVVGNVP--ELAPAAAYI
Zea mais                     AG-EPFLPGFEGVASPGAAD-----YGLSRFDHIVGNVP--ELAPAAAYF
Arabidopsis thaliana         TEKSEFLPGFERVEDASSFP-LD--YGIRRLDHAVGNVP--ELGPALTYV
Daucus carota                G---LFLPGFEAVEGTASFPDLD--YGIRRLDHAVGNVT--ELGPVVEYI
Streptomyces avermitilis     G---PYLPGYVAAA---PIVEPPAHRTFQAIDHCVGNVELGRMNEWVGFY
Pseudomonas fluorescens      S--SIYDIDFVFLEGVDRHP-VG--AGLKIIDHLTHNVYRGRMAYWANFY
                                 :  .:                 :  :** . *    .:      :
                                  !         !            !         !
P. fluorescens numbering         140       150          160       170

Mus musculus                 LKNLQFHRFWSVDDTQVHTEYSSLRSIVVTNYEESIKMPINEPAPG-RKK
Coccidioides immitis         EKILGFHRFWSVDDKDICTEFSALKSIVMASPNDIVKMPINEPAKG-KKQ
Mycosphaerella graminicola   ERCLGFHRFWSVDDKDICTEFSALKSIVMSSPNQVVKMPINEPAHG-KKK
Hordeum vulgare              AGFTGFHEFAEFTAEDVGTTESGLNSVVLANNSEGVLLPLNEPVHGTKRR
Zea mais                     AGFTGFHEFAEFTTEDVGTAESGLNSMVLANNSENVLLPLNEPVHGTKRR
Arabidopsis thaliana         AGFTGFHQFAEFTADDVGTAESGLNSAVLASNDEMVLLPINEPVHGTKRK
Daucus carota                KGFTGFHEFAEFTAEDVGTLESGLNSVVLANNEEMVLLPLNEPVYGTKRK
Streptomyces avermitilis     NKVMGFTNMKEFVGDDIATEYSALMSKVVADGTLKVKFPINEPALA-KKK
Pseudomonas fluorescens      EKLFNFREIRYF---DIKGEYTGLTSKAMTAPDGMIRIPLNEESSK--GA
                                  * .:  .   ::   :.* * .::    :  :*:**
                             !         !            !         !        .!
P. fluorescens numbering    180       190          200       210       220
```

FIG 1 (continuation)

```
Mus musculus              SQIQEYVDYNGGAGVQHIALKTEDIITAIRHLRER---GTEFLAAP-SS
Coccidioides immitis      SQIEEYVDFYNGAGVQHIALRTNNIIDAITNLKAR---GTEFIKVP-ET
Mycosphaerella graminicola SQIEEYVDFYNGPGVQHIALRTPNIIEAVSNLRSR---GVEFISVP-DT
Hordeum vulgare           SQIQTFLEHHGPGVQHIAVASSDVLRTLRKMRARSAMGGFDFLPPPLPK
Zea mais                  SQIQTFLDHHGPGVQHMALASDDVLRTLREMQARSAMGGFEFMAPPTSD
Arabidopsis thaliana      SQIQTYLEHNEGAGLQHLAIMSEDIFRTLREMRKRSSIGGFDFMPSPPPT
Daucus carota             SQIQTYLEHNEGAGVQHLALVSEDIFRTLREMRKRSCLGGFEFMPSPPPT
Streptomyces avermitilis  SQIDEYLEFYGGAGVQHIALNTGDIVETVRTMRAA---GVQFLDTP-DS
Pseudomonas fluorescens   GQIEEFLMQFNGEGIQHVAPLSDDLIKTWDHLKSI---GMRFMTAPPDT
                          .*: ::  *  *:***:*.  : ::.:   :  :       *   *:  *
                               230       240       250       260       270
P. fluorescens numbering Mus musculus              YYKLLRENLKSAKIQVKESMDVLEELHILVD-YDEKG---YLLQIFTKPM
Coccidioides immitis      YYEDMKIRLKRQGLVLDEDFETLKSLDILID-FDENG---YLLQLFTKHL
Mycosphaerella graminicola YYENMRLRLKAAGMKLEESSFDIIQKLNILID-FDEGG---YLLQLFTKPL
Hordeum vulgare           YYEGVRRLAG--DVLSEAQIKECQELGVLVD-RDDQG---VLLQIFTKPV
Zea mais                  :GVRRRAG--EVLTEAQIKECQELGVLVD-RDDQG---VLLQIFTKPV
Arabidopsis thaliana      YY:NLKKRVG--DVLSDDQIKECEELGILVD-RDDQG---TLLQIFTKPL
Daucus carota             YYKNLKNRVG--DVLSDEQIKECEDIGILVD-RDDQG---TLLQIFTKPV
Streptomyces avermitilis  YYDTLGEWVG----DTRVPVDTLRELKILAD-RDEDG---YLLQIFTKPV
Pseudomonas fluorescens   YYEMLEGRLP----NHGEPVGELQARGILDGSSESGDKRLLLQIFSETL
                          **. :          :  :   *:   *.         : **:*:*:  :
                                280       290       300       310
P. fluorescens numbering Mus musculus              QDRPTLFLEVIQR--------H------NHQGFGAGNFNSLFKAFEE-E
Coccidioides immitis      MDRPTLTVFIEIIQR-------N------NFSGFGAGNFRALFEAIER-E
Mycosphaerella graminicola MDRPTVFIEIIQR--------N------NFDGFGAGNFKSLFEAIER-E
Hordeum vulgare           GDRPTLFLEMIQRIGCMEKDERGEEYQKGCGGFGKGNFSELFKSIEDYE
Zea mais                  GDRPTLFLEIIQRIGCMEKDEKGQEYQKGCGGFGKGNFSQLFKSIEDYE
Arabidopsis thaliana      GDRPTIFIEIIQRVGCMMKDEEGKAYQSGCGGFGKGNFSELFKSIEEYE
Daucus carota             GDRPTLFIEIIQRVGCMLKDDAGQMYQKGCGGFGKGNFSELFKSIEEYE
Streptomyces avermitilis  QDRPTVFFEIIER--------H------GSMGFGKGNFKALFEAIER-E
Pseudomonas fluorescens   MG--PVFFEFIQR--------K------GDDGFGEGNFKALFESIER-D
                          .  :*:.*.*:*          ***  ***  ****  **::::*:    :
                                    320         330         340
P. fluorescens numbering FIG 1 (continuation)
```

| | | |
|---|---|---|
| Mus musculus | QALRGNLTDLEPNGVRSGM | (SEQ ID NO:14) |
| Coccidioides immitis | QALRGTLI----------- | (SEQ ID NO:13) |
| Mycosphaerella graminicola | QDLRGNL----------- | (SEQ ID NO:12) |
| Hordeum vulgare | KSLEAKQS---AAVQGS-- | (SEQ ID NO:11) |
| Zea mais | KSLEAKQAAAPAAAQGS-- | (SEQ ID NO:10) |
| Arabidopsis thaliana | KTLEAKQLVG--------- | (SEQ ID NO:9) |
| Daucus carota | KTLEAKQITGSAAA----- | (SEQ ID NO:8) |
| Streptomyces avermitilis | QEKRGNL----------- | (SEQ ID NO:7) |
| Pseudomonas fluorescens | NTRRGVLSTD--------- | (SEQ ID NO:6) |

P. fluorescens numbering  :  350

FI

SEQUENCE LISTING

<160> NUMBER OF SEQ ID NOS: 14

<210> SEQ ID NO 1
<211> LENGTH: 26
<212> TYPE: DNA
<213> ORGANISM: Mus musculus

<400> SEQUENCE: 1

-continued ccgattaacg aaccggtgca cggaac     26

<210> SEQ ID NO 2
<211> LENGTH: 27
<212> TYPE: DNA
<213> ORGANISM: Mus musculus

<400> SEQUENCE: 2
cccttgaatg aaccggtgta tgggacc     27

<210> SEQ ID NO 3
<211> LENGTH: 27
<212> TYPE: DNA
<213> ORGANISM: Mus musculus

<400> SEQUENCE: 3
ctaatcctgt taccgttggc tgctgcc     27

<210> SEQ ID NO 4
<211> LENGTH: 27
<212> TYPE: DNA
<213> ORGANISM: Mus musculus

<400> SEQUENCE: 4
ccgctcaacg aaccggtgca cggcacc     27

<210> SEQ ID NO 5
<211> LENGTH: 27
<212> TYPE: DNA
<213> ORGANISM: Mus musculus

<400> SEQUENCE: 5
gcagttgctc gtcgacaagc tctgtcc     27

<210> SEQ ID NO 6
<211> LENGTH: 358
<212> TYPE: PRT
<213> ORGANISM: Pseudomonas fluorescens

<400> SEQUENCE: 6

Met Ala Asp Leu Tyr Glu Asn Pro Met Gly Leu Met Gly Phe Glu Phe
 1               5                  10                  15

Ile Glu Leu Ala Ser Pro Thr Pro Asn Thr Leu Glu Pro Ile Phe Glu
             20                  25                  30

Ile Met Gly Phe Thr Lys Val Ala Thr His Arg Ser Lys Asp Val His
         35                  40                  45

Leu Tyr Arg Gln Gly Ala Ile Asn Leu Ile Leu Asn Asn Glu Pro His
     50                  55                  60

Ser Val Ala Ser Tyr Phe Ala Ala Glu His Gly Pro Ser Val Cys Gly
 65                  70                  75                  80

Met Ala Phe Arg Val Lys Asp Ser Gln Lys Ala Tyr Lys Arg Ala Leu
                 85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Phe
    130                 135                 140

Leu Glu Gly Val Asp Arg His Pro Val Gly Ala Gly Leu Lys Ile Ile

```
                145                 150                 155                 160
Asp His Leu Thr His Asn Val Tyr Arg Gly Arg Met Ala Tyr Trp Ala
                    165                 170                 175

Asn Phe Tyr Glu Lys Leu Phe Asn Phe Arg Glu Ile Arg Tyr Phe Asp
                180                 185                 190

Ile Lys Gly Glu Tyr Thr Gly Leu Thr Ser Lys Ala Met Thr Ala Pro
                195                 200                 205

Asp Gly Met Ile Arg Ile Pro Leu Asn Glu Glu Ser Ser Lys Gly Ala
                210                 215                 220

Gly Gln Ile Glu Glu Phe Leu Met Gln Phe Asn Gly Glu Gly Ile Gln
225                 230                 235                 240

His Val Ala Phe Leu Ser Asp Asp Leu Ile Lys Thr Trp Asp His Leu
                245                 250                 255

Lys Ser Ile Gly Met Arg Phe Met Thr Ala Pro Pro Asp Thr Tyr Tyr
                260                 265                 270

Glu Met Leu Glu Gly Arg Leu Pro Asn His Gly Glu Pro Val Gly Glu
                275                 280                 285

Leu Gln Ala Arg Gly Ile Leu Leu Asp Gly Ser Ser Glu Ser Gly Asp
                290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
                340                 345                 350

Gly Val Leu Ser Thr Asp
                355

<210> SEQ ID NO 7
<211> LENGTH: 380
<212> TYPE: PRT
<213> ORGANISM: Streptomyces avermitilis

<400> SEQUENCE: 7

Met Thr Gln Thr Thr His His Thr Pro Asp Thr Ala Arg Gln Ala Asp
1               5                   10                  15

Pro Phe Pro Val Lys Gly Met Asp Ala Val Phe Ala Val Gly Asn
                20                  25                  30

Ala Lys Gln Ala Ala His Tyr Ser Thr Ala Phe Gly Met Gln Leu Val
            35                  40                  45

Ala Tyr Ser Gly Pro Glu Asn Gly Ser Arg Glu Thr Ala Ser Tyr Val
        50                  55                  60

Leu Thr Asn Gly Ser Ala Arg Phe Val Leu Thr Ser Val Ile Lys Pro
65                  70                  75                  80

Ala Thr Pro Trp Gly His Phe Leu Ala Asp His Val Ala Glu His Gly
                85                  90                  95

Asp Gly Val Val Asp Leu Ala Ile Glu Val Pro Asp Ala Arg Ala Ala
                100                 105                 110

His Ala Tyr Ala Ile Glu His Gly Ala Arg Ser Val Ala Glu Pro Tyr
            115                 120                 125

Glu Leu Lys Asp Glu His Gly Thr Val Val Leu Ala Ala Ile Ala Thr
        130                 135                 140

Tyr Gly Lys Thr Arg His Thr Leu Val Asp Arg Thr Gly Tyr Asp Gly
145                 150                 155                 160
```

```
Pro Tyr Leu Pro Gly Tyr Val Ala Ala Pro Ile Val Glu Pro Pro
            165                 170                 175

Ala His Arg Thr Phe Gln Ala Ile Asp His Cys Val Gly Asn Val Glu
            180                 185                 190

Leu Gly Arg Met Asn Glu Trp Val Gly Phe Tyr Asn Lys Val Met Gly
            195                 200                 205

Phe Thr Asn Met Lys Glu Phe Val Gly Asp Asp Ile Ala Thr Glu Tyr
            210                 215                 220

Ser Ala Leu Met Ser Lys Val Val Ala Asp Gly Thr Leu Lys Val Lys
225                 230                 235                 240

Phe Pro Ile Asn Glu Pro Ala Leu Ala Lys Lys Ser Gln Ile Asp
            245                 250                 255

Glu Tyr Leu Glu Phe Tyr Gly Gly Ala Gly Val Gln His Ile Ala Leu
            260                 265                 270

Asn Thr Gly Asp Ile Val Glu Thr Val Arg Thr Met Arg Ala Ala Gly
            275                 280                 285

Val Gln Phe Leu Asp Thr Pro Asp Ser Tyr Tyr Asp Thr Leu Gly Glu
            290                 295                 300

Trp Val Gly Asp Thr Arg Val Pro Val Asp Thr Leu Arg Glu Leu Lys
305                 310                 315                 320

Ile Leu Ala Asp Arg Asp Glu Asp Gly Tyr Leu Leu Gln Ile Phe Thr
            325                 330                 335

Lys Pro Val Gln Asp Arg Pro Thr Val Phe Glu Ile Ile Glu Arg
            340                 345                 350

His Gly Ser Met Gly Phe Gly Lys Gly Asn Phe Lys Ala Leu Phe Glu
            355                 360                 365

Ala Ile Glu Arg Glu Gln Glu Lys Arg Gly Asn Leu
            370                 375                 380

<210> SEQ ID NO 8
<211> LENGTH: 442
<212> TYPE: PRT
<213> ORGANISM: Daucus carota

<400> SEQUENCE: 8

Met Gly Lys Lys Gln Ser Glu Ala Glu Ile Leu Ser Ser Asn Ser Ser
 1               5                  10                  15

Asn Thr Ser Pro Ala Thr Phe Lys Leu Val Gly Phe Asn Asn Phe Val
                20                  25                  30

Arg Ala Asn Pro Lys Ser Asp His Phe Ala Val Lys Arg Phe His His
            35                  40                  45

Ile Glu Phe Trp Cys Gly Asp Ala Thr Asn Thr Ser Arg Arg Phe Ser
        50                  55                  60

Trp Gly Leu Gly Met Pro Leu Val Ala Lys Ser Asp Leu Ser Thr Gly
65                  70                  75                  80

Asn Ser Val His Ala Ser Tyr Leu Val Arg Ser Ala Asn Leu Ser Phe
                85                  90                  95

Val Phe Thr Ala Pro Tyr Ser Pro Ser Thr Thr Thr Ser Ser Gly Ser
            100                 105                 110

Ala Ala Ile Pro Ser Phe Ser Ala Ser Gly Phe His Ser Phe Ala Ala
            115                 120                 125

Lys His Gly Leu Ala Val Arg Ala Ile Ala Leu Glu Val Ala Asp Val
130                 135                 140

Ala Ala Ala Phe Glu Ala Ser Val Ala Arg Gly Ala Arg Pro Ala Ser
145                 150                 155                 160
```

```
Ala Pro Val Glu Leu Asp Asp Gln Ala Trp Leu Ala Glu Val Glu Leu
            165                 170                 175

Tyr Gly Asp Val Val Leu Arg Phe Val Ser Phe Gly Arg Glu Glu Gly
            180                 185                 190

Leu Phe Leu Pro Gly Phe Glu Ala Val Glu Gly Thr Ala Ser Phe Pro
            195                 200                 205

Asp Leu Asp Tyr Gly Ile Arg Arg Leu Asp His Ala Val Gly Asn Val
            210                 215                 220

Thr Glu Leu Gly Pro Val Val Glu Tyr Ile Lys Gly Phe Thr Gly Phe
225                 230                 235                 240

His Glu Phe Ala Glu Phe Thr Ala Glu Asp Val Gly Thr Leu Glu Ser
            245                 250                 255

Gly Leu Asn Ser Val Val Leu Ala Asn Asn Glu Met Val Leu Leu
            260                 265                 270

Pro Leu Asn Glu Pro Val Tyr Gly Thr Lys Arg Lys Ser Gln Ile Gln
            275                 280                 285

Thr Tyr Leu Glu His Asn Glu Gly Ala Gly Val Gln His Leu Ala Leu
            290                 295                 300

Val Ser Glu Asp Ile Phe Arg Thr Leu Arg Glu Met Arg Lys Arg Ser
305                 310                 315                 320

Cys Leu Gly Gly Phe Glu Phe Met Pro Ser Pro Pro Thr Tyr Tyr
            325                 330                 335

Lys Asn Leu Lys Asn Arg Val Gly Asp Val Leu Ser Asp Glu Gln Ile
            340                 345                 350

Lys Glu Cys Glu Asp Leu Gly Ile Leu Val Asp Arg Asp Gln Gly
            355                 360                 365

Thr Leu Leu Gln Ile Phe Thr Lys Pro Val Gly Asp Arg Pro Thr Leu
            370                 375                 380

Phe Ile Glu Ile Ile Gln Arg Val Gly Cys Met Leu Lys Asp Asp Ala
385                 390                 395                 400

Gly Gln Met Tyr Gln Lys Gly Gly Cys Gly Gly Phe Gly Lys Gly Asn
            405                 410                 415

Phe Ser Glu Leu Phe Lys Ser Ile Glu Glu Tyr Glu Lys Thr Leu Glu
            420                 425                 430

Ala Lys Gln Ile Thr Gly Ser Ala Ala Ala
            435                 440

<210> SEQ ID NO 9
<211> LENGTH: 445
<212> TYPE: PRT
<213> ORGANISM: Arabidopsis thaliana

<400> SEQUENCE: 9

Met Gly His Gln Asn Ala Ala Val Ser Glu Asn Gln Asn His Asp Asp
 1               5                  10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45

His Ile Glu Phe Trp Cys Gly Asp Ala Thr Asn Val Ala Arg Arg Phe
         50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
```

```
                    85                  90                  95
Phe Leu Phe Thr Ala Pro Tyr Ser Pro Ser Leu Ser Ala Gly Glu Ile
                100                 105                 110

Lys Pro Thr Thr Thr Ala Ser Ile Pro Ser Phe Asp His Gly Ser Cys
                115                 120                 125

Arg Ser Phe Phe Ser Ser His Gly Leu Gly Val Arg Ala Val Ala Ile
                130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
                180                 185                 190

Lys Ala Glu Asp Thr Glu Lys Ser Glu Phe Leu Pro Gly Phe Glu Arg
                195                 200                 205

Val Glu Asp Ala Ser Ser Phe Pro Leu Asp Tyr Gly Ile Arg Arg Leu
                210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
                260                 265                 270

Asn Asp Glu Met Val Leu Leu Pro Ile Asn Glu Pro Val His Gly Thr
                275                 280                 285

Lys Arg Lys Ser Gln Ile Gln Thr Tyr Leu Glu His Asn Glu Gly Ala
290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
                340                 345                 350

Val Leu Ser Asp Asp Gln Ile Lys Glu Cys Glu Glu Leu Gly Ile Leu
                355                 360                 365

Val Asp Arg Asp Gln Gly Thr Leu Leu Gln Ile Phe Thr Lys Pro
                370                 375                 380

Leu Gly Asp Arg Pro Thr Ile Phe Ile Glu Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
                420                 425                 430

Glu Tyr Glu Lys Thr Leu Glu Ala Lys Gln Leu Val Gly
                435                 440                 445

<210> SEQ ID NO 10
<211> LENGTH: 444
<212> TYPE: PRT
<213> ORGANISM: Zea mays

<400> SEQUENCE: 10

Met Pro Pro Thr Pro Thr Ala Ala Ala Gly Ala Ala Val Ala Ala
1               5                   10                  15
```

```
Ala Ser Ala Ala Glu Gln Ala Ala Phe Arg Leu Val Gly His Arg Asn
        20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
        50                  55                  60

Phe Ser Phe Gly Leu Gly Ala Pro Leu Ala Ala Arg Ser Asp Leu Ser
 65                  70                  75                  80

Thr Gly Asn Ser Ala His Ala Ser Leu Leu Arg Ser Gly Ser Leu
                85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
            130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
            245                 250                 255

Leu Asn Ser Met Val Leu Ala Asn Asn Ser Lys Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Met Ala Leu Ala
        290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
            325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
            355                 360                 365

Leu Leu Gln Ile Phe Thr Lys Pro Val Gly Asp Arg Pro Thr Leu Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Ser Gln Leu Phe Lys Ser Ile Glu Asp Tyr Glu Lys Ser Leu Glu Ala
            420                 425                 430

Lys Gln Ala Ala Ala Ala Ala Ala Gln Gly Ser
```

<210> SEQ ID NO 11
<211> LENGTH: 434
<212> TYPE: PRT
<213> ORGANISM: Hordeum vulgare

<400> SEQUENCE: 11

```
Met Pro Pro Thr Pro Thr Thr Pro Ala Ala Thr Gly Ala Ala Ala
 1               5                  10                  15

Val Thr Pro Glu His Ala Arg Pro His Arg Met Val Arg Phe Asn Pro
                20                  25                  30

Arg Ser Asp Arg Phe His Thr Leu Ser Phe His His Val Glu Phe Trp
            35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
                100                 105                 110

Ser Ala Asp Ala Ala Arg Arg Phe Ser Ala Asp His Gly Ile Ala Val
            115                 120                 125

Arg Ser Val Ala Leu Arg Val Ala Asp Ala Ala Glu Ala Phe Arg Ala
        130                 135                 140

Ser Arg Arg Gly Ala Arg Pro Ala Phe Ala Pro Val Asp Leu Gly
145                 150                 155                 160

Arg Gly Phe Ala Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
                195                 200                 205

Phe Asp His Val Val Gly Asn Val Pro Glu Leu Ala Pro Ala Ala Ala
    210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Gly Val Leu Leu Pro Leu Asn Glu Pro Val His Gly
                260                 265                 270

Thr Lys Arg Arg Ser Gln Ile Gln Thr Phe Leu Glu His Gly Gly
                275                 280                 285

Pro Gly Val Gln His Ile Ala Val Ala Ser Ser Asp Val Leu Arg Thr
        290                 295                 300

Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
                340                 345                 350

Leu Val Asp Arg Asp Asp Gln Gly Val Leu Leu Gln Ile Phe Thr Lys
                355                 360                 365
```

-continued

Pro Val Gly Asp Arg Pro Thr Leu Phe Leu Glu Met Ile Gln Arg Ile
    370             375             380

Gly Cys Met Glu Lys Asp Glu Arg Gly Glu Glu Tyr Gln Lys Gly Gly
385                 390             395                 400

Cys Gly Gly Phe Gly Lys Gly Asn Phe Ser Glu Leu Phe Lys Ser Ile
                405             410             415

Glu Asp Tyr Glu Lys Ser Leu Glu Ala Lys Gln Ser Ala Ala Val Gln
            420             425             430

Gly Ser

<210> SEQ ID NO 12
<211> LENGTH: 419
<212> TYPE: PRT
<213> ORGANISM: Mycosphaerella graminicola

<400> SEQUENCE: 12

Met Ala Pro Gly Ala Leu Leu Val Thr Ser Gln Asn Gly Arg Thr Ser
1               5                   10                  15

Pro Leu Tyr Asp Ser Asp Gly Tyr Val Pro Ala Pro Ala Ala Leu Val
            20                  25                  30

Val Gly Gly Glu Val Asn Tyr Arg Gly Tyr His His Ala Glu Trp Trp
        35                  40                  45

Val Gly Asn Ala Lys Gln Val Ala Gln Phe Tyr Ile Thr Arg Met Gly
    50                  55                  60

Phe Glu Pro Val Ala His Lys Gly Leu Glu Thr Gly Ser Arg Phe Phe
65                  70                  75                  80

Ala Ser His Val Val Gln Asn Asn Gly Val Arg Phe Val Phe Thr Ser
                85                  90                  95

Pro Val Arg Ser Ser Ala Arg Gln Thr Leu Lys Ala Ala Pro Leu Ala
            100                 105                 110

Asp Gln Ala Arg Leu Asp Glu Met Tyr Asp His Leu Asp Lys His Gly
        115                 120                 125

Asp Gly Val Lys Asp Val Ala Phe Glu Val Asp Asp Val Leu Ala Val
    130                 135                 140

Tyr Glu Asn Ala Val Ala Asn Gly Ala Glu Ser Val Ser Ser Pro His
145                 150                 155                 160

Thr Asp Ser Cys Asp Glu Gly Asp Val Ile Ser Ala Ala Ile Lys Thr
                165                 170                 175

Tyr Gly Asp Thr Thr His Thr Phe Ile Gln Arg Thr Thr Tyr Thr Gly
            180                 185                 190

Pro Phe Leu Pro Gly Tyr Arg Ser Cys Thr Thr Val Asp Ser Ala Asn
        195                 200                 205

Lys Phe Leu Pro Pro Val Asn Leu Glu Ala Ile Asp His Cys Val Gly
    210                 215                 220

Asn Gln Asp Trp Asp Glu Met Ser Asp Ala Cys Asp Phe Tyr Glu Arg
225                 230                 235                 240

Cys Leu Gly Phe His Arg Phe Trp Ser Val Asp Asp Lys Asp Ile Cys
                245                 250                 255

Thr Glu Phe Ser Ala Leu Lys Ser Ile Val Met Ser Ser Pro Asn Gln
            260                 265                 270

Val Val Lys Met Pro Ile Asn Glu Pro Ala His Gly Lys Lys Lys Ser
        275                 280                 285

Gln Ile Glu Glu Tyr Val Asp Phe Tyr Asn Gly Pro Gly Val Gln His
    290                 295                 300

-continued

```
Ile Ala Leu Arg Thr Pro Asn Ile Ile Glu Ala Val Ser Asn Leu Arg
305                 310                 315                 320

Ser Arg Gly Val Glu Phe Ile Ser Val Pro Asp Thr Tyr Tyr Glu Asn
                325                 330                 335

Met Arg Leu Arg Leu Lys Ala Ala Gly Met Lys Leu Glu Glu Ser Phe
            340                 345                 350

Asp Ile Ile Gln Lys Leu Asn Ile Leu Ile Asp Phe Asp Glu Gly Gly
        355                 360                 365

Tyr Leu Leu Gln Leu Phe Thr Lys Pro Leu Met Asp Arg Pro Thr Val
    370                 375                 380

Phe Ile Glu Ile Ile Gln Arg Asn Asn Phe Asp Gly Phe Gly Ala Gly
385                 390                 395                 400

Asn Phe Lys Ser Leu Phe Glu Ala Ile Glu Arg Glu Gln Asp Leu Arg
                405                 410                 415

Gly Asn Leu

<210> SEQ ID NO 13
<211> LENGTH: 399
<212> TYPE: PRT
<213> ORGANISM: Coccidioides immitis

<400> SEQUENCE: 13

Met Ala Pro Ala Ala Asp Ser Pro Thr Leu Gln Pro Ala Gln Pro Ser
  1               5                  10                  15

Asp Leu Asn Gln Tyr Arg Gly Tyr Asp His Val His Trp Tyr Val Gly
             20                  25                  30

Asn Ala Lys Gln Ala Ala Thr Tyr Tyr Val Thr Arg Met Gly Phe Glu
         35                  40                  45

Arg Val Ala Tyr Arg Gly Leu Glu Thr Gly Ser Lys Ala Val Ala Ser
     50                  55                  60

His Val Val Arg Asn Gly Asn Ile Thr Phe Ile Leu Thr Ser Pro Leu
 65                  70                  75                  80

Arg Ser Val Glu Gln Ala Ser Arg Phe Pro Glu Asp Glu Ala Leu Leu
                 85                  90                  95

Lys Glu Ile His Ala His Leu Glu Arg His Gly Asp Gly Val Lys Asp
            100                 105                 110

Val Ala Phe Glu Val Asp Cys Val Glu Ser Val Phe Ser Ala Ala Val
        115                 120                 125

Arg Asn Gly Ala Glu Val Val Ser Asp Val Arg Thr Val Glu Asp Glu
    130                 135                 140

Asp Gly Gln Ile Lys Met Ala Thr Ile Arg Thr Tyr Gly Glu Thr Thr
145                 150                 155                 160

His Thr Leu Ile Glu Arg Ser Gly Tyr Arg Gly Gly Phe Met Pro Gly
                165                 170                 175

Tyr Arg Met Glu Ser Asn Ala Asp Ala Thr Ser Lys Phe Leu Pro Lys
            180                 185                 190

Val Val Leu Glu Arg Ile Asp His Cys Val Gly Asn Gln Asp Trp Asp
        195                 200                 205

Glu Met Glu Arg Val Cys Asp Tyr Tyr Glu Lys Ile Leu Gly Phe His
    210                 215                 220

Arg Phe Trp Ser Val Asp Asp Lys Asp Ile Cys Thr Glu Phe Ser Ala
225                 230                 235                 240

Leu Lys Ser Ile Val Met Ala Ser Pro Asn Asp Ile Val Lys Met Pro
                245                 250                 255
```

-continued

```
Ile Asn Glu Pro Ala Lys Gly Lys Lys Gln Ser Gln Ile Glu Glu Tyr
            260                 265                 270

Val Asp Phe Tyr Asn Gly Ala Gly Val Gln His Ile Ala Leu Arg Thr
        275                 280                 285

Asn Asn Ile Ile Asp Ala Ile Thr Asn Leu Lys Ala Arg Gly Thr Glu
    290                 295                 300

Phe Ile Lys Val Pro Glu Thr Tyr Tyr Glu Asp Met Lys Ile Arg Leu
305                 310                 315                 320

Lys Arg Gln Gly Leu Val Leu Asp Glu Asp Phe Glu Thr Leu Lys Ser
                325                 330                 335

Leu Asp Ile Leu Ile Asp Phe Asp Glu Asn Gly Tyr Leu Leu Gln Leu
            340                 345                 350

Phe Thr Lys His Leu Met Asp Arg Pro Thr Val Phe Ile Glu Ile Ile
        355                 360                 365

Gln Arg Asn Asn Phe Ser Gly Phe Gly Ala Gly Asn Phe Arg Ala Leu
    370                 375                 380

Phe Glu Ala Ile Glu Arg Glu Gln Ala Leu Arg Gly Thr Leu Ile
385                 390                 395

<210> SEQ ID NO 14
<211> LENGTH: 393
<212> TYPE: PRT
<213> ORGANISM: Mus musculus

<400> SEQUENCE: 14

Met Thr Thr Tyr Asn Asn Lys Gly Pro Lys Pro Glu Arg Gly Arg Phe
1               5                   10                  15

Leu His Phe His Ser Val Thr Phe Trp Val Gly Asn Ala Lys Gln Ala
            20                  25                  30

Ala Ser Phe Tyr Cys Asn Lys Met Gly Phe Glu Pro Leu Ala Tyr Arg
        35                  40                  45

Gly Leu Glu Thr Gly Ser Arg Glu Val Val Ser His Val Ile Lys Arg
    50                  55                  60

Gly Lys Ile Val Phe Val Leu Cys Ser Ala Leu Asn Pro Trp Asn Lys
65                  70                  75                  80

Glu Met Gly Asp His Leu Val Lys His Gly Asp Gly Val Lys Asp Ile
            85                  90                  95

Ala Phe Glu Val Glu Asp Cys Asp His Ile Val Gln Lys Ala Arg Glu
        100                 105                 110

Arg Gly Ala Lys Ile Val Arg Glu Pro Trp Val Glu Gln Asp Lys Phe
    115                 120                 125

Gly Lys Val Lys Phe Ala Val Leu Gln Thr Tyr Gly Asp Thr Thr His
130                 135                 140

Thr Leu Val Glu Lys Ile Asn Tyr Thr Gly Arg Phe Leu Pro Gly Phe
145                 150                 155                 160

Glu Ala Pro Thr Tyr Lys Asp Thr Leu Leu Pro Lys Leu Pro Arg Cys
                165                 170                 175

Asn Leu Glu Ile Ile Asp His Ile Val Gly Asn Gln Pro Asp Gln Glu
            180                 185                 190

Met Gln Ser Ala Ser Glu Trp Tyr Leu Lys Asn Leu Gln Phe His Arg
        195                 200                 205

Phe Trp Ser Val Asp Asp Thr Gln Val His Thr Glu Tyr Ser Ser Leu
    210                 215                 220

Arg Ser Ile Val Val Thr Asn Tyr Glu Glu Ser Ile Lys Met Pro Ile
225                 230                 235                 240
```

-continued

```
Asn Glu Pro Ala Pro Gly Arg Lys Lys Ser Gln Ile Gln Glu Tyr Val
            245                 250                 255

Asp Tyr Asn Gly Gly Ala Gly Val Gln His Ile Ala Leu Lys Thr Glu
            260                 265                 270

Asp Ile Ile Thr Ala Ile Arg His Leu Arg Glu Arg Gly Thr Glu Phe
            275                 280                 285

Leu Ala Ala Pro Ser Ser Tyr Tyr Lys Leu Leu Arg Glu Asn Leu Lys
            290                 295                 300

Ser Ala Lys Ile Gln Val Lys Glu Ser Met Asp Val Leu Glu Glu Leu
305                 310                 315                 320

His Ile Leu Val Asp Tyr Asp Glu Lys Gly Tyr Leu Leu Gln Ile Phe
                325                 330                 335

Thr Lys Pro Met Gln Asp Arg Pro Thr Leu Phe Leu Glu Val Ile Gln
            340                 345                 350

Arg His Asn His Gln Gly Phe Gly Ala Gly Asn Phe Asn Ser Leu Phe
            355                 360                 365

Lys Ala Phe Glu Glu Glu Gln Ala Leu Arg Gly Asn Leu Thr Asp Leu
    370                 375                 380

Glu Pro Asn Gly Val Arg Ser Gly Met
385                 390
```

CHIMERIC HYDROXYL-PHENYL PYRUVATE DIOXYGENASE, DNA SEQUENCE AND METHOD FOR OBTAINING PLANTS CONTAINING SUCH A GENE, WITH HERBICIDE TOLERANCE

FIELD OF THE INVENTION

The present invention relates to a nucleic acid sequence encoding a chimeric hydroxyphenylpyruvate dioxygenase (HPPD), a chimeric gene comprising this sequence as encoding sequence, and its use for obtaining plants which are resistant to certain herbicides.

BACKGROUND

The hydroxyphenylpyruvate dioxegenases are enzymes which catalyse the transformation reaction of parahydroxyphenylpyruvate (HIPP) into homogentisate. This reaction takes place in the presence of iron ($FE^{2+}$) and in the presence of oxygen (Crouch N.P. et al., Tetrahedron, 53, 20, 6993–7010, 1997). We may put forward the hypothesis that the HPPDs contain an active site which is suitable of catalyzing this reaction, in which the iron, the substrate and the water molecule combine, even though such an active site has never been described to date.

Moreover, there are also known certain molecules which inhibit this enzyme and which attach themselves competitively to the enzyme to inhibit the transformation of HPP into homogentisate. It has been found that some of these molecules can be used as herbicides, insofar as the inhibition of the reaction in the plants leads to bleaching of the leaves of the treated plants and to the death of these plants (Pallett K. E. et al., 1997, Pestic. Sci. 50 83–84). Such herbicides of the prior art which target HPPD are, in particular, the isoxazoles (EP 418 175, EP 470 856, EP 487 352, EP 527 036, EP 560 482, EP 682 659, U.S. Pat. No. 5,424,276), in particular isoxaflutole, which is a selective maize herbicide, the diketonitriles (EP 496 630, EP 496 631) in particular 2-cyano-3-cyclopropyl-1-(2-$SO_2CH_3$-4-$CF_3$-phenyl)-propane-1,3-dione and 2-cyano-3-cyclopropyl-1-(2-$SO_2CH_3$-4-2,3-$Cl_2$-phenyl)-propane-1,3-dione, the triketones (EP 625 505, EP 625 508, U.S. Pat. No. 5,506,195), in particular sulcotrione, or else the pyrazolinates., To make the plants herbicide-tolerant, three principal strategies are available, viz. (1) making the herbicide non-toxic using an enzyme which transforms the herbicide or its active metabolite into non-toxic degradation products, such as, for example, the enzymes for tolerance to bromoxynil or to Basta (EP 242 236, EP 337 899); (2) conversion of the target enzyme into a functional enzyme which is less sensitive to the herbicide or its active metabolite, such as, for example, the enzymes for tolerance to glyphosate (EP 293 356, Padgette S. R. et al., J. Biol. Chem., 266, 33, 1991); or (3) overexpression of the sensitive enzyme, in such a way that the plant produces high enough quantities of the target enzyme with regard to the kinetic constants of this enzyme relative to the herbicide in such a way that it has enough functional enzyme despite the presence of its inhibitor.

With this third strategy, it has been described that plants which are tolerant to HPPD inhibitors (WO 96/38567) were successfully obtained, it being understood that a simple strategy of overexpressing the sensitive (unaltered) target enzyme was successfully employed for the first time to impart to the plants a herbicide tolerance which is at an agronomical level.

Despite the success obtained with this simple strategy of overexpressing the target enzyme, the system for HPPD inhibitor tolerance must be varied to obtain tolerance whatever the culture conditions of the tolerant plants or the commercial doses of herbicide application in the field. It is known from the prior art (WO 96/38567) that enzymes of different origin (plants, bacteria, fungi) have primary protein sequences which differ substantially and that these enzymes have an identical function and essentially similar or related kinetic characteristics.

It has now been found that all these HPPDs have, on the one hand, many sequence homologies in their C-terminal portion (FIG. 1) and, on the other hand, an essentially similar tertiary (three-dimensional) structure (FIG. 2). As regards the competitive inhibition characteristic, the hypothesis is put forward that the HPPD inhibitors attach themselves to the enzyme at the active site of the latter, or in its vicinity, in such a way that the access of HPP to this active site is blocked and its conversion in the presence of iron and of water is prevented. It has now been found that, by mutating the enzyme in its C-terminal portion, it was possible to obtain functional HPPDs which are less sensitive to HPPD inhibitors, so that their expression in the plants allows an improved HPPD inhibitor tolerance. As regards these elements, it can thus be concluded that the active site of the enzyme is located in its C-terminal portion, while its N-terminal portion essentially ensures its stability and its oligomerization (Pseudomonas HPPD is a tetramer, plant HPPDs are dimers).

SUMMARY OF THE INVENTION

It has now been found that it was possible to generate a chimeric enzyme by combining the N-tenninal portion of a first enzyme with the C-terminal position of a second enzyme so as to obtain a novel functional chimeric HPPD, which allows each portion to be selected for its particular properties, such as, for example, to select the N-terminal portion of a first enzyme for its stability properties in a given cell (plant, bacterium and the like) and the C-terminal portion of a second enzyme for its kinetic properties (activity, inhibitor tolerance, and the like).

The present invention therefore primarily relates to a chimeric HPPD which, while being functional, that is to say retaining its properties of catalysing the conversion of HPP into homogentisate, comprises the N-terminal portion of a first HPPD in combination with the C-terminal portion of a second HPPD.

DESCRIPTION OF THE DRAWINGS

FIG. 1 is an alignment of HPPD amino acid sequences.

DETAILED DESCRIPTION

Figure 2:
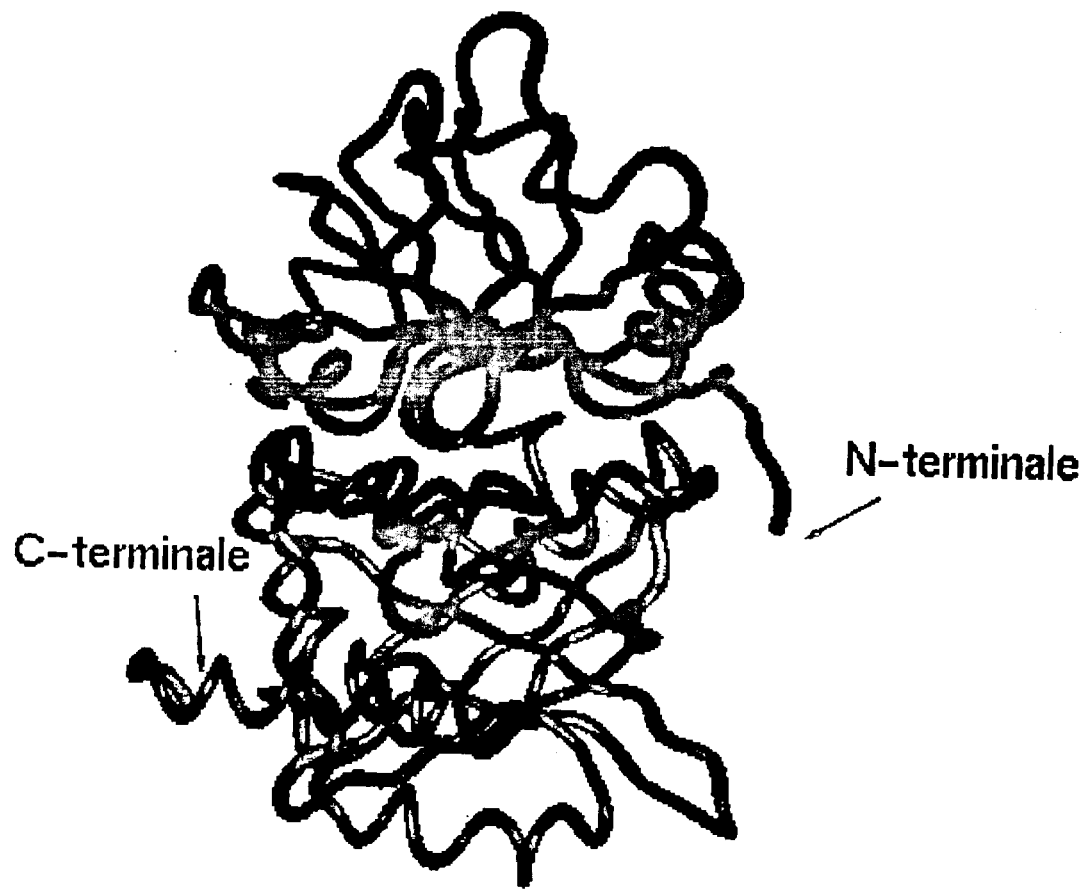
FIG. 2 is a representation of an HPPD tertiary structure.

Each portion of the chimeric HPPD according to the invention is derived from an HPPD of any origin and is, in particular, selected from amongst plant, bacterial or fungal HPPDs.

According to a preferred embodiment of the invention, the N-terminal portion of the chimeric HPPD. is derived from -Slant HPPD, this plant preferably being chosen from dicots, in particular, *Arabidopsis thaliana* or *Daucus carota*, or else from monocots, such as maize or wheat.

According to another preferred embodiment of the invention, the C-terminal portion of the chimeric HPPD is derived from a plant HPPD as defined above or from an HPPD of a microorganism, especially a bacterium, in particular Pseudomonas, more particularly Pseudomonas fluorescens, or of a fungus, it being possible for this C-terminal portion to be natural or mutated by substituting one or more amino acids of the C-terminal portion of the original HPPD, especially for making it less sensitive to HPPD inhibitors.

A number of HPPDs and their primary sequence have been described in the prior art, especially HPPDs from bacteria such as Pseudomonas (Rüetschi et al., Eur. J. Biochem., 205, 459–466, 1992, WO 96/38567), plants such as Arabidopsis (WO 96/38567, Genebank AF047834) or carrot (WO 96/38567, Genebank 87257), from Coccicoides (Genebank COITRP), or mammals such as mouse or pig.

Since the alignment of these sequences is known through the usual methods of the art, for example the method described by Thompson, J. D. et al. (CLUSTAL W: Improving the sensitivity of progressive multiple sequence alignment through sequence weighting, positions-specific gap penalties and weight matrix choice, Nucleic Acids Research, 22:4673–46800, 1994) and through access to these computer programs for sequence alignment, for example via internet, the person skilled in the art can define sequence homologies relative to a reference sequence and recognize the key amino acids, or else define the regions which they have in common, which especially allows a C-terminal region and an N-terminal region to be defined on the basis of this reference sequence.

The reference sequence for the present invention is the sequence from Pseudomonas, SEQ ID NO: 6, and all definitions and indications of specific amino acid positions relate to the primary sequence of Pseudomonas HPPD, (SEQ ID NO: 6). The appended FIG. 1 shows an alignment of a plurality of HPPD sequences which are described in the prior art and which are aligned relative to the Pseudomonas HPPD sequence (SEQ ID NO: 6) by way of reference; they include the HPPD sequence of *Streptomyces avermitilis*, SEQ ID NO: 7 (GenBank SAV11864), of *Daucus carota*, SEQ ID NO: 8 (GenBank DCU87257), of *Arabidopsis thaliana*, SEQ ID NO: 9 (GenBank AF047834), of *Zea mays*, SEQ ID NO: 10, of *Hordeum vulgare*, SEQ ID NO: 11 (GenBank HVAJ693), of *Mycosphaerella grarninicola*, SEQ ID NO: 12 (GenBank AF038152), of *Coccicoides imrnitis*, SEQ ID NO: 13 (GenBank COITRP), and of Mus musculus, SEQ ID NO: 14 (GenBank MU54HD). This figure shows the numbering of the amuno acids of the Pseudomonas sequence (SEQ ID NO: 6), and the amino acids which they have in common are designated by an asterisk. Based on such an alignment, and with the definition of the Pseudomonas amino acid, (SEQ ID NO: 6), it is easy to identify the position of the corresponding amino acid in a different HPPD sequence by its position and its nature (the alignment of sequences of different origin, viz, plants, mammals and bacteria, demonstrate that this alignment method, which is well known to those skilled in the art, can be applied generally to any other sequence).

The C-terminal portion of the HPPDs, which is where the active site of the enzyme is located, differs from its N-terminal portion by a linkage peptide, as shown by the schematic diagram of the tertiary structure of the Pseudomonas HPPD monomer given in FIG. 2. This structure was obtained by the usual methods of crystal X-ray diffraction analysis. The linkage peptide will allow the N-terminal end of the C-terminal portion of the enzyme to be defined, this peptide being located between amino acids 145 and 157 in the case of Pseudomonas, SEQ ID NO: 6 (cf. FIG. 1).

The C-terminal portion can thus be defined as being composed of the sequence which is delimited, on the one hand, by the linkage peptide and, on the other hand, by the C-terminal end of the enzyme. The sequence alignment shown in the appended FIG. 1 demonstrated for all sequences two amino acids in positions 161 and 162 in the case of the Pseudomonas sequence (D=Asp161 and H=His162). Relative to the Pseudomonas HPPD, it can thus be defined that the linkage peptide which, represents the N-terminal end of the C-terminal portion of the HPPD is located approximately between 5 and 15 amino acids upstream of the amino acid Asp161.

The present invention equally relates to a nucleic acid sequence encoding an above-described chimeric HPPD. According to the present invention, "nucleic acid sequence" is to be understood as being a nucleotide sequence which can be of the DNA or the RNA type, preferably of the DNA type, especially double-stranded whether it is of natural or synthetic origin, especially a DNA sequence for which the codons encoding the chimeric HPPD according to the invention will have been optimized according to the host organism in which it will be expressed, these optimization methods being well known to those skilled in the art.

The sequences encoding each HPPD derived from the chimeric HPPD according to the invention can be of any origin. In particular, it can be of bacterial origin. Bacteria of the following types can be mentioned as specific examples: Pseudomonas sp., for example *Pseudomonas fluorescens* or else cyanobacteria of the type Synechocystis. The origin of the sequence can also be a plant, especially it may be derived from dicots such as tobacco, Arabidopsis, Umbelliferae such as *Daucus carota*, or else monocots such as *Zea mays* or wheat. The encoding sequences and the means of isolating and cloning them are described in the abovementioned references, whose contents are incorporated herein by reference.

The encoding sequences of the N-terminal and C-terminal portions of the chimeric HPPD according to the invention can be assembled by any usual method for constructing and assembling nucleic acid fragments which are well known to those skilled in the art and widely described in the literature and illustrated especially by the use examples of the invention.

The present invention therefore also relates to a process of generating a nucleic acid sequence encoding a chimeric HPPD according to the invention, this process being defined hereinabove.

Another subject of the invention is the use of a nucleic acid sequence encoding a chimeric HPPD according to the invention in a process for the transformation of plants, as marker gene or as encoding sequence which allows a tolerance to HPPD inhibitor herbicides to be imparted to the plant. It is well understood that this sequence can also be used in combination with another marker gene, or marker genes, and/or a sequence, or sequences, encoding one or more agronomic properties.

The present invention also relates to a chimeric gene (or expression cassette) comprising an encoding sequence as well as heterologous regulatory elements in positions 5' and 3' which can function in a host organism, in particular plant cells or plants, the encoding sequence comprising at least one nucleic acid sequence encoding a chimeric HPPD as defined above.

By host organism there is to be understood any single-celled or lower or higher multi-celled organism into which the chimeric gene according to the invention can be introduced so as to produce chimeric HPPD. In particular, these are bacteria, for example *E. coli*, yeasts, in particular of the genera Saccharomyces or Kluyveromyces, Pichia, fungi, in particular Aspergillus, a baculovirus, or, preferably, plant cells and plants.

By plant cell, there is to be understood according to the invention any plant-derived cell which can constitute indifferentiated tissues, such as calli, differentiated tissues such as embryos, parts of plants, plants or seeds.

By plant there is to be understood according to the invention any differentiated multi-celled organism which can photosynthesize in particular monocots or dicots, more particularly crop plants for animal or human nutrition or non-food crop plants, such as maize, wheat, oilseed rape, soya, rice, sugar cane, beet, tobacco, cotton and the like.

The regulatory elements required for expressing the nucleic acid sequence encoding an HPPD, are well knownto those skilled in the art and depend on the host organism. They comprise, in particular, promoter sequences, transcription activators, terminator sequences, inclusive of start and stop codons. The means and methods for identifying and choosing the regulatory elements are well known to those skilled in the art and widely described in the literature.

More particularly, the invention relates to the transformation of plants. Any regulatory promoter sequence of a gene which is expressed naturally in plants, in particular a promoter which is expressed particularly in the leaves of plants, such as, for example, so-called constitutive promoters derived from bacteria, viruses or plants such as, for example, a histone promoter as described in Application EP 0 507 698, or a rice actin promoter, of a plant virus gene, such as, for example, that of cauliflower mosaic virus (CAMV 19S or 35S), or else so-called light-dependent promoters such asthat of a gene of the FUJI small subunit of ribulose biscarboxylase/oxygenase (Rubisco) of a plant, or any other suitable known promoter can be used as regulatory promoter sequence in plants.

In combination with the regulatory promoter sequence, it is also possible to use, in accordance with the invention, other regulatory sequences which are located between the promoter and the encoding sequence, such as transcription activators (enhancers), such as, for example, the tobacco mosaic virus (TMV) translation activator described in Application WO 87/07644 or the tobacco etch virus (TEV) translation activator described by Carrington & Freed.

As regulatory terminator or polyadenylation sequence, there can be used any corresponding sequence derived from bacteria, such as, for example, the *Agrobacterium tumefaciens* nos terminator, or else derived from plants, such as, for example, a histone terminator as described in Application EP 0 633 317.

According to a particular embodiment of the invention, at the 5'-position of the nucleic acid sequence encoding a chimeric HPPD there is employed a nucleic acidsequence encoding a leader peptide, this sequence being located between the promoter region and the sequence encoding the chimeric HPPD in such a manner as to allow expression of a fusion protein of leader peptide/chimeric HPPD, the latter being as defined above. The leader peptide allows the chimeric HPPD to be sent to the plastids, more particularly the chloroplasts, the fusion protein being cleaved between the leader peptide and the chimeric HPPD as it passes through the plastid membrane. The leader peptide can be simple, such as an EPSPS leader peptide (described in U.S. Pat. No. 5,188,642) or a leader peptide of that of the small ribulose biscarboxylase/oxygenase subunit (ssu Rubisco) of a plant, which may comprise some amino acids of the N-terminal portion of the mature ssu Rubisco (EP 189 707) or else a multiple leader peptide comprising a first plant leader peptide fused with a portion of the N-terminal sequence of a mature protein localized in the plastids which is fused to a second plant leader peptide as described in Patent EP 508 909, and more particularly the optimized leader peptide comprising a sunflower ssu Rubisco leader peptide fused to 22 amino acids of the N-terminal end of maize ssu Rubisco fused to the leader peptide of maize ssu Rubisco as described together with the encoding sequence in Patent EP 508 909.

The present invention also relates to the fusion protein of leader peptide/chimeric HPPD, the two elements of this fusion protein being defined further above.

The present invention also relates to a cloning and/or expression vector for transforming a host organism containing at least one chimeric gene as defined hereinabove. This vector comprises, in addition, to the above chimeric gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature. To transform plant cells or plants, this will be, in particular, a virus which may be employed for transforming developed plants and furthermore contains its own replication and expression elements. The transformation vector for plant cells or plants according to the invention is preferably a plasmid.

A further subject of the invention is a process for the transformation of host organisms, in particular plant cells, by integrating at least one nucleic acid sequence or chimeric gene as defined hereinabove, which transformation may be carried out by any suitable known means which have been widely described in the specialist literature and in particular in the references cited in the present application, more particularly by the vector according to the invention.

One series of methods consists of bombarding cells, protoplasts or tissues with particles to which the DNA sequences have been attached. Another series of methods consists in using a chimeric gene inserted into an *Agrobacterium tumefaciens* Ti plasmid or *Agribacterium rhizogenes* Ri plasmid as transfer means into the plant. Other methods can be used, such as microinjection or electroporation, or else direct precipitation with PEG. The person skilled in the art will choose the appropriate method according to the nature of the host organism, in particular of the plant cell or the plant.

A further subject of the present invention are host organisms, in particular plant cells or plants, which are transformed and contain a chimeric gene comprising a sequence encoding a chimeric HPPD as defined hereinabove.

A further subject of the present invention are the plants which comprise transformed cells, in particular the plants regenerated from transformed cells. Regeneration is effected by any suitable process, which depends on the nature of the species as described, for example, in the references hereinabove. Patents and patent applications which are cited in particular for the processes for transforming plant cells and regenerating plants are the following: U.S. Pat. Nos. 4,459,355, 4,536,475, 5,464,763, 5,177,010, 5,187,073, EP 267, 159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174, EP 486 233, EP 486 234, EP 539 563, EP 674 725, WO 91/02071 and WO 95/06128.

The present invention also relates to the transformed plants obtained from growing and/or hybridizing regenerated plants hereinabove as well as to the seeds of transformed plants.

The transformed plants which can be obtained according to the invention can be of the monocotyledonous type such as, for example, cereals, sugar cane, rice and maize, or of the dicotyledonous type such as, for example, tobacco, soya, oilseed rape, cotton, beet, clover and the like.

Another subject of the invention is a method of selectively controlling weeds in plants, in particular crops, with the aid of an HPPD inhibitor, in particular a herbicide defined hereinabove, characterized in that this herbicide is applied to transformed plants according to the invention, either pre-planting, pre-emergence or post-emergence of the crop.

The present invention also relates to a method of controlling weeds at the surface of a field with seeds or plants transformed with the chimeric gene according to the invention, the process consisting in applying, to this surface of the field, a dose of an HPPD inhibitor herbicide which is toxic to these weeds, without, however, substantially affecting the seeds or plants transformed with this chimeric gene according to the invention.

The present invention also relates to a method of growing plants which have been transformed according to the invention with a chimeric gene according to the invention, the method consisting in planting the seeds of these transformed plants at a surface of a field which is suitable for growing these plants, in applying, if weeds are present, to this surface of this field a dose of a herbicide which targets the HPPD defined hereinabove and which is,toxic to the weeds, without substantially affecting these seeds or these transformed plants, and then in harvesting the grown plants when they achieve the desired maturity and, finally, in separating the seeds from the harvested plants.

In the two above methods, the herbicide which targets HPPD can be applied according to the invention, either pre-planting, pre-emergence or post-emergence of the crop.

Herbicide is to be understood as meaning for the purposes of the present invention a herbicidally active substance alone or in combination with an additive which modifies its efficacy such as, for example, an agent which increases the activity (synergist) or limits the activity (safener). The HPPD inhibitor herbicides are in particular previously defined. Of course, the above herbicides are combined in a manner known per se with the formulation auxiliaries conventionally used in agrochemistry for their practical application.

When the transformed plant according to the invention comprises another tolerance gene for another herbicide (such as, for example, a gene encoding a chimeric or non-chimeric EPSPS which imparts glyphosate tolerance to the plant), or when the transformed plant is naturally insensitive to another herbicide, the process according to the invention may comprise the simultaneous or staggered application of an HPPD inhibitor in combination with said herbicide, for example glyphosate.

Another object of the invention is the use of the chimeric gene encoding a chimeric HPPD as marker gene during the transformation regeneration cycle of a plant species and selection based on the above herbicide.

The different aspects of the invention will be understood better with reference to the experimental examples which follow.

All the methods or operations described hereinbelow in these examples are given by way of example and represent a choice between the various methods which are available for arriving at the same result. This choice has no effect on the quality of the result and, as a consequence, any suitable method may be used by the person skilled in the-art to arrive at the same result. Most of the DNA fragment engineering methodsare described in "Current Protocols in Molecular Biology" Volumes 1 and 2, Ausubel F.M. et al., which are published by Greene Publishing Associates and Wiley-Interscience (1989), or in Molecular cloning, T. Maniatis, E. F. Fritsch, J. Sambrook, 1982.

EXAMPLE 1

Colorimetric Screening Test for Mutants which are Tolerant to 2-cyano-3-cyclopropyl-1-(2-$SO_2$-$CH_3$-4-$CF_3$-phenyl)-propane-1,3-dione pRP C: The vector pRP A (which is described in the application WO 96/38567), which contains a genomic DNA fragment and the encoding region of the *Pseudomonas fluorescens* A32 HPPD gene, was digested with NcoI, purified and then ligated into the expression vector pKK233-2 (Clontech) which itself had been digested with NcoI, the only cloning site of this vector. The orientation of the gene in the resulting vector pRP C, which allows expression under-the control of the trc promoter, was checked.

A YT-broth-type culture medium with 1% agarose (Gibco BRL ultra pure) and 5 mM L-tyrosine (Sigma), which contains the selection agent for the above vector pRP C is poured into 96-well plates at 100 $\mu$l per well. 10 $\mu$l of an *E. coli* culture in the exponential growth phase which contains the vector pRP C is applied to each well. After 16 hours at 37° C., the wells which do not contain the culture medium or those which have been seeded with an *E. coli* culture containing the vector PKK233-2 are transparent, while the wells seeded with an *E. coli* culture containing the vector pRP C are brown.

A series was established with identical culture medium containing different concentrations (0 mM to 14 mM) of 2-cyano-3-cyclopropyl-1-(2-methylsulphonyl-4-trifluoromethylphenyl)-propane-i,3-dione (EP 0 496 631) which was solubilized in water and brought to pH 7.5. This molecule is a diketonitrile, known as an efficient inhibitor of HPPD activity (Pallett, K. E. et al. 1997. Pestic. Sci. 50, 83–84). In the bacterial culture containing the vector pRP C, a total absence of staining is observed for 7 mM of the above compound.

Identical results were obtained when 2-cyano-3-cyclopropyl-1-(2-methyl-4-trifluoromethylphenyl)propane-1,3-dione was substituted by 2-cyano-3-cyclopropyl-1-(2-methylsulphonyl-4-(methylthio)phenyl)-propane-1,3-dione and 2-(2-chloro-3-ethoxy-4-(ethyl-sulphonyl)benzoyl)-5-methyl-1,3-cyclohexadione, (WO 93/03009). The end concentrations of the two molecules in DMSO solution are 3.5 mM and 7 mM, respectively.

These results confirm that a test based on the HPPD activity, whatever the origin of this activity, allows the identification of HPPD activities which present a tolerance to HPPD activity inhibitors from the family of the isoxazolesas well as the triketones.

EXAMPLE 2

Preparation and Evaluation of the Activity of Chimeric HPPDS

The purpose is to generate fusions between HPPDs of phylogenetically different organisms, such as monocotyledonous and dicotyledonous plants or bacteria, with the following advantages:

HPPDs are obtained whose characteristics in terms of codon usage are more advantageous for the expression in hosts where a tolerance to HPPD inhibitors is desirable, but difficult to obtain with a non-chimeric HPPD, HPPDs are obtained whose characteristics in terms of weak affinity to the inhibitors are more advantageous, an HPPD activity is obtained in vitro or in vivo with a gene which is interesting, but of which no partial clone is available.

The fusions of N- and C-terminal domains of plants were tested.

1) Construction

Fusions were carried out between the N-terminal regions of dicots and the C-terminal region of maize. These regions were introduced into dicots, which are phylogenetically related.

The search for the fusion zone was based on comparisons of protein sequences of different HPPDs (FIG. 1). By homology with the *Pseudomonas fluorescens* HPPD, SEQ ID NO: 6, the N-terminal portions of *Arabidopsis thaliana*, SEQ ID NO: 9, and of *Daucus carota*, SEQ ID NO: 8, were identified; they terminate with tyrosine 219 and tyrosine 212, respectively. The partial gene of *Zea mays*, SEQ ID NO: 10, thus corresponds to 80% of the C-terminal portion of the protein.

The PINEP region, which is highly conserved in plants, was chosen as the exchange zone. Upstream there is the N-terminal portion, and downstream there is the C-terminal portion. By studying nucleotide sequences, it has been attempted to introduce a restriction site, if possible a single restriction site, which modifies the protein sequence in this region little or not at all. The AgeI restriction site, which meets these criteria, can be obtained by modifying the codon usage for the adjacent amino acids E and P.

The AgeI site was introduced by directed mutagenesis using the USE method for the *Arabidopsis thaliana* (SEQ ID NO: 9) and *Daucus carota* (SEQ ID NO: 8) HPPD, with the aid of the degenerated oligonucleotides AgeAra and AgeCar, and with the USE selection oligonucleotide AlwNI, which can be used with vector pTRC.

```
                                              (SEQ ID NO:1)
AgeAra     5'pCCGATTAACGAACCGGTGCACGGAAC 3'

(SEQ ID NO:2)
AgeCar     5'pCCCTTGAATGAACCGGTGTATGGGACC 3'

(SEQ ID NO:3)
USE AlwNI  5'pCTAATCCTGTTACCGTTGGCTGCTGCC 3'
```

PCR mutagenesis was used to introduce simultaneously the SalI site at the end of the gene and the AgeI site in *Zea mays* (SEQ ID NO: 10) so as to facilitate subcloning of all the fusions in the same vector at the same sites. The primers used are AgeMaïs and SalMaïsRev.

```
                                              (SEQ ID NO:4)
AgeMais
5'CCGCTCAACGAACCGGTGCACGGCACC 3'

(SEQ ID NO:5)
SalMaisRev
5'GCAGTTGCTCGTCGACAAGCTCTGTCC 3'
```

After replacing the AgeI/SalI fragment of the *Arabidopsis thaliana* HPPD (SEQ ID NO: 9) clone with the *Zea mays* (SEQ ID NO: 10) or *Daucus carota* (SEQ ID NO: 8) AgeI/SalI. fragment, clones are obtained which encode chimeric *Arabidopsis thaliana*/*Zea mays* and *Arabidopsis thaliana*/*Daucus carota* HPPDs, which are termed pFAM and pFAC, respectively (which stands for fusion of the N-terminal of *Arabidopsis thaliana* (SEQ ID NO: 9) with a C-terminal of maize or of carrot). Similarly, clones pFCM and pFCA were obtained with the *Daucus carota* HPPD (SEQ ID NO: 8) clone.

2) in Vivo Activity

The brown staining of the isolated colonies that reflects the.HPPD activity was observed for the fusions FAM, FAC, FCA and FCM. The brown staining was scored on a scale from 1 to 10, 10 being the most intense (as described in Example 1), by comparison with HPPDs derived from *Arabidopsis thaliana* (FAA) and *Daucus carota* (FCC).

| N-terminal fragment | C-terminal fragment | | |
|---|---|---|---|
| | **C | **M | **A |
| FC* | 5 | 2 | 2 |
| FA* | 9 | 9 | 10 |

In general, the activity drops for each fusion in comparison with the HPPD which provides the complete N-terminal domain at the beginning of the C-terminal domain.

Where the N-terminal originates from *Arabidopsis thaliana* (SEQ ID NO: 9), the drop in activity is slight, but where the N-terminal originates from *Daucus carota* (SEQ ID NO: 8), the activity measured drops more markedly.

However, these experiments demonstrate that the chimeric hppds are active enzymes and that it is currently quite possible to express these chimeras in plants and, for example, to express an hppd with an N-terminal derived from dicots and a C-terminal derived from monocots in the plants.

What is claimed is:

1. A nucleic acid encoding a chimeric HPPD, which chimeric HPPD comprises the N-terminal portion of a first plant HPPD in combination with the C-terminal portion of a second plant HPPD, and wherein the N-termlinal portion and the C-terminal portion are separated by a linker peptide.

2. The nuleic acid of claim 1, wherein the N-terminal portion of a first plant HPPD is of dicot plant origin.

3. The nucleic acid of claim 2, wherein the dicot plant is *Arabidopsis thaliana* or *Daucus carota*.

4. The nucleic acid of claim 1, wherein the N-terminal portion of a first plant HPPD is of monocot plant origin.

5. The nucleic acid of claim 4, wherein the monocot plant is wheat or maize.

6. The nucleic acid of claim 1, wherein the C-terminal portion of a second plant HPPD is of dicot plant origin.

7. The nucleic acid of claim 6, wherein the dicot plant is *Arabidopsis thaliana* or *Daucus carota*.

8. The nucleic acid of claim 1, wherein the C-terminal portion of a second plant HPPD is of monocot plant origin.

9. The nucleic acid of claim 8, wherein the monocot plant is wheat or maize.

10. A chimeric gene comprising in operable linkage the nucleic acid of claim 1 and regulatory elements functional in a host organism, wherein the regulatory elements comprise a promoter from a gene that is expressed in the host organism and at least one polyadenylation sequence.

11. The chimeric gene according to claim 10, wherein the regulatory elements are functional in a plant cell or plant.

12. The chimeric gene according to claim 11 further comprising a nucleic acid encoding a plant leader peptide wherein said chimeric gene encodes a fusion protein comprising a leader peptide and chimeric HPPD.

13. The chimeric gene according to claim 11, further comprising a nucleic acid encoding a transit peptide between the promoter and the nucleic acid encoding the chimeric HPPD.

14. The chimeric gene according to claim 11, further comprising a transcription enhancer sequence between the promoter and the nucleic acid encoding the chimeric HPPD.

15. A cloning vector comprising the chimeric gene of claim 10.

16. An expression vector comprising the chimeric gene of claim 10.

17. A process for transforming a host cell, comprising stably integrating the nucleic acid of claim 1 or the chimeric gene of claim 10 into the host cell.

18. The process according to claim 17, wherein the host cell is a plant cell.

19. The process of claim 18, further comprising regenerating a plant from the plant cell.

20. An isolated host cell transformed with the nucleic acid according to claim 1 or the chimeric gene according to claim 10.

21. A plant cell which contains the nucleic acid according to claim 1 or the chimeric gene according to claim 10.

22. A plant which contains the nucleic acid according to claim 1 or the chimeric gene according to claim 10.

23. A plant regenerated from the cell of claim 21, or a transgenic plant obtained by crossing said plant with another plant.

24. The plant according to claim 22 or claim 23, which is selected from the group consisting of sugar cane, rice and maize.

25. The plant according to claim 22 or claim 23, which is selected from the group consisting of tobacco, soya, oilseed rape, cotton, beet and clover.

26. Transgenic seed of the plant according to claim 22 or claim 23.

27. Transgenic seed of the plant according to claim 24.

28. Transgenic seed of the plant according to claim 25.

29. A process of controlling weeds in a field which comprises applying an HPPD inhibitor herbicide to a field which contains weeds and;

a) seeds which contain a nucleic acid encoding a chimeric HPPD, which chimeric HPPD comprises the N-terminal portion of a first plant HPPD in combination with the C-terminal portion of a second plant HPPD wherein the N-terminal portion and the C-terminal portion are separated by a linker peptide; or b) plants which contain a nucleic acid encoding a chimeric HPPD, which chimeric HPPD comprises the N-terminal portion of a first plant HPPD in combination with the C-terminal portion of a second plant HPPD wherein the N-terminal portion and the C-terminal portion are separated by a linker peptide wherein said weeds in said field are controlled by said HPPD inhibitor herbicide.

30. The process of claim 29, further comprising harvesting the plants and separating the seeds from the harvested plants.

31. The process of claim 29, wherein the HPPD herbicide inhibitor is selected from the group consisting of isoxazoles, diketonitriles, triketones, and pyrazolinates.

32. The process of claim 30, wherein the HPPD herbicide inhibitor is isoxaflutole.

33. The process of claim 30, wherein the HPPD herbicide inhibitor is selected from the group consisting of 2-cyano-3-cyclopropyl-1-(2-SO2CH3-4-CF3-phenyl)-propane-1,3-dione and 2-cyano-3-cyclopropyl-1-(2-SO2CH3-4-2,3-Cl2-phenyl)-propane-1,3-dione.

34. The process according to claim 30, wherein the HPPD herbicide inhibitor is sulcotrione.

* * * * *

UNITED STATES PATENT AND TRADEMARK OFFICE
CERTIFICATE OF CORRECTION

PATENT NO. : 6,768,044 B1
DATED : July 27, 2004
INVENTOR(S) : Philippe Boudec et al.

It is certified that error appears in the above-identified patent and that said Letters Patent is hereby corrected as shown below:

Column 31,
Line 34, "N-termlinal" should read -- N-terminal --.

Signed and Sealed this

Twenty-third Day of November, 2004

JON W. DUDAS
*Director of the United States Patent and Trademark Office*